(12) United States Patent
Borchert et al.

(10) Patent No.: US 6,888,011 B2
(45) Date of Patent: May 3, 2005

(54) POROUS CATALYST FOR THE HYDROGENATION OF MALEIC ANHYDRIDE TO TETRAHYDROFURAN

(75) Inventors: Holger Borchert, Offstein (DE); Stephan Schlitter, Limburgerhof (DE); Markus Rösch, Oppenheim (DE); Rolf-Hartmuth Fischer, Heidelberg (DE); Ralf-Thomas Rahn, Mannheim (DE); Alexander Weck, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 146 days.

(21) Appl. No.: 10/433,012

(22) PCT Filed: Dec. 7, 2001

(86) PCT No.: PCT/EP01/14392

§ 371 (c)(1),
(2), (4) Date: May 29, 2003

(87) PCT Pub. No.: WO02/47818

PCT Pub. Date: Jun. 20, 2002

(65) Prior Publication Data

US 2004/0030163 A1 Feb. 12, 2004

(30) Foreign Application Priority Data

Dec. 11, 2001 (DE) .......................................... 100 61 553

(51) Int. Cl.⁷ .............................................. C07D 307/08
(52) U.S. Cl. ..................................................... 549/508
(58) Field of Search ......................................... 549/508

(56) References Cited

U.S. PATENT DOCUMENTS

| | | |
|---|---|---|
| 3,065,243 A | 11/1962 | Dunlop et al. |
| 3,580,930 A | 5/1971 | Miya et al. |
| 4,006,165 A | 2/1977 | Michalczyk et al. |
| 5,072,009 A | 12/1991 | Budge et al. |
| 5,122,495 A | 6/1992 | Taylor et al. |
| 5,149,836 A | 9/1992 | DeThomas et al. |
| 5,155,086 A | 10/1992 | Thakur et al. |
| 5,453,412 A | 9/1995 | Deckers et al. |
| 5,536,849 A | 7/1996 | Bergfeld et al. |
| 5,591,873 A | 1/1997 | Bankmann et al. |
| 6,008,375 A | 12/1999 | Bergfeld et al. |
| 6,124,234 A | 9/2000 | Fetzer et al. |
| 6,153,161 A | 11/2000 | Fetzer et al. |

FOREIGN PATENT DOCUMENTS

| | | |
|---|---|---|
| DE | 143 01 469 | 7/1994 |
| DE | 195 46612 | 6/1997 |
| EP | 604 792 | 7/1994 |
| EP | 638 565 | 2/1995 |
| EP | 656 336 | 6/1995 |
| EP | 669 163 | 8/1995 |
| EP | 1 108 702 | 6/2001 |
| WO | 95/225539 | 8/1995 |
| WO | 97/24346 | 7/1997 |
| WO | 97/34694 | 9/1997 |
| WO | 99/35139 | 7/1999 |
| WO | 99/38856 | 8/1999 |

OTHER PUBLICATIONS

Derwent Abst. JP 2233–631.
Jrl. of Porous Materials, 2, 79–84 (1995).

Primary Examiner—Bernard Dentz
(74) Attorney, Agent, or Firm—Novak Druce & Quigg, LLP

(57) ABSTRACT

A hydrogenation catalyst which is suitable, in particular, for the hydrogenation of maleic anhydride and its derivatives to THF or its derivatives comprises copper oxide and at least one further metal or compound thereof, preferably an oxide, selected from the group consisting of Al, Si, Zn, La, Ce, the elements of groups IIIA to VIIIA and the elements of groups IA and IIA and having a pore volume of $\geq 0.01$ ml/g for pore diameters of >50 nm and a ratio of the pore volume of macropores having a diameter of >50 nm to the total pore volume for pores having a diameter of >4 nm of >10%.

19 Claims, No Drawings

POROUS CATALYST FOR THE HYDROGENATION OF MALEIC ANHYDRIDE TO TETRAHYDROFURAN

This application is a 371 of PCT/EP01/14392 filed Dec. 7, 2001.

The present invention relates to a process for preparing unsubstituted or alkyl-substituted γ-butyrolactone and tetrahydrofuran by catalytic hydrogenation in the gas phase of substrates selected from the group consisting of maleic acid and succinic acid and derivatives of these acids. For the purposes of the present invention, derivatives are esters and anhydrides which, like the acids themselves, may bear one or more alkyl substituents. A catalyst having a specific porosity is used.

The preparation of γ-butyrolactone (GBL) and tetrahydrofuran (THF) by gas-phase hydrogenation of maleic anhydride (MA) is a reaction which has been known for many years. Numerous catalyst systems for carrying out this catalytic reaction are described in the literature. Many of these are Cr-containing. Depending on the composition of the catalyst and the reaction parameters chosen, different product distributions are obtained using such catalysts.

Apart from MA, further possible starting materials for preparing GBL and THF are maleic acid itself, succinic acid and its anhydride and also the esters of these acids. If GBL and THF bearing alkyl substituents are to be prepared, the alkyl-substituted species corresponding to the abovementioned acids, esters and anhydrides can be used.

U.S. Pat. No. 3,065,243 discloses a process in which copper chromite is employed as catalyst. According to the description and examples, this reaction results in formation of considerable amounts of succinic anhydride (SA) which has to be circulated. As is known, process engineering problems due to crystallization of SA or succinic acid formed therefrom with subsequent blocking of pipes frequently occur.

Further copper chromite catalysts for the hydrogenation of MA are disclosed, for example, in U.S. Pat. Nos. 3,580,930, 4,006,165, EP-A 638 565 and WO 99/38856. According to the disclosures, high yields of GBL can be achieved using the catalysts described there. THF is in each case formed only in traces. However, larger amounts of THF are often desired for a number of reasons.

A process which allows this is disclosed in U.S. Pat. No. 5,072,009. The catalysts used according to this patent have the formula $Cu_1Zn_bAl_cM_dO_x$ in which M is at least one element selected from the group consisting of the elements of groups IIA and IIIA, VA, VIII, Ag, Au, the elements of groups IIIB to VIIB and the lanthanides and actinides of the Periodic Table of the Elements, b is from 0.001 to 500, c is from 0.001 to 500 and d is from 0 to <200 and x corresponds to the number of oxygen atoms necessary according to valence criteria. Although it is stated that the catalysts used according to this patent do not have to contain any chromium, all the examples describe chromium-containing catalysts. According to these examples, the maximum THF yield obtained is 96%, and the hydrogenation is carried out at from 20 to 40 bar.

A two-stage catalyst system for the hydrogenation of MA is described in U.S. Pat. No. 5,149,836. The catalyst for the first stage is chromium-free while the catalyst for the second stage is based on Cu—Zn—Cr oxides.

An in-principle disadvantage of all the above-described catalyst systems is the presence of chromium oxide, whose use should be avoided because of the acute toxicity. Cr-free catalyst systems for preparing GBL by hydrogenation of MA are also described in the prior art. Examples of such catalyst systems may be found in WO 99/35139 (Cu—Zn oxide), WO 95/22539 (Cu—Zn—Zr) and U.S. Pat. No. 5,122,495 (Cu—Zn—Al oxide). All these catalyst systems make it possible to achieve high yields of GBL, up to 98%, but only traces of THF, if any, are formed. Although the formation of the latter can, as is apparent, be favored by increasing the reaction temperature or by longer residence times in the reactor, the proportion of undesirable by-products, for example butanol, butane, ethanol or ethane, increases at the same time.

A catalyst made up exclusively of copper oxide and aluminum oxide for the gas-phase hydrogenation of MA to form GBL is disclosed in WO 97/24346. This catalyst, too, suffers from the same disadvantages as those described in the publications listed in the previous paragraph, namely only minor or trace formation of THF.

The use of a catalyst having in principle the same composition as described in WO 97/24346, namely based on Cu—Al oxides, is also disclosed in JP 2 233 631. The object of that invention is to carry out the hydrogenation of MA in such a way that THF and 1,4-butanediol are formed as main products and only small amounts, if any, of GBL are formed. This is achieved by use of catalysts based on mixed Cu—Al oxides and by adherence to particular reaction conditions. Typical mixtures obtained using this process comprise from about 15 to 20 mol % of 1,4-butanediol and from 60 to 80 mol % of THF, and the amount of THF can even be increased to over 99 mol % according to one example. This is achieved by using a large excess of GBL as solvent. However, if no solvent is employed, the THF yields drop considerably to values of about 75%.

A feature common to all the catalysts disclosed in the above-mentioned publications is that they have a uniform structure. The components present are intimately mixed with one another, as a result of which the structure becomes essentially homogeneous and the catalyst has no substantial constituents having different structures.

In contrast, EP-A 0 404 408 discloses a catalyst for the hydrogenation of MA, whose structure is in principle different than that of the catalysts in the abovementioned references. The catalytically active material corresponds essentially to the material disclosed in the above-cited U.S. Pat. No. 5,072,009. The material is then applied to an essentially inert, at least partly porous support having an outer surface. The catalytically active material adheres to the outer surface of the support. In contrast to the corresponding catalyst which is not applied to a support and gives THF as main product, this supported catalyst gives GBL as preferred product together with large amounts of SA as by-product. It is stated in the description that when using the same active material in the form of an all-active catalyst, as disclosed in U.S. Pat. No. 5,079,009, THF formation is favored as the size of the shaped catalyst body increases. However, higher GBL yields are obtained when using a coated catalyst in which the catalytically active material is applied in the form of a thin layer to the support.

In Journal of Porous Materials, 2 (1995), pages 79 to 84, Castiglioni et al. report that the porosity of copper oxide/zinc oxide/aluminum oxide catalysts is reduced by repeated pressing. Pressing in this way results in catalysts which have a higher selectivity to THF in the hydrogenation of MA, while the formation of GBL drops.

It is generally known that the diffusion paths of the reacting components in the pores of the catalytically active composition of a coated catalyst are shorter than in the case of an all-active catalyst consisting of the same material. The results found hitherto for the hydrogenation of maleic anhydride using catalysts of different porosities accordingly teach a person skilled in the art that short diffusion paths in a catalyst favor the formation of GBL while long diffusion paths promote the formation of THF. This also appears plausible since THF is formed in the hydrogenation as subsequent product of the GBL initially formed.

Surprisingly, it has now been possible to develop catalysts which are based on copper oxide and have a high proportion of macropores and which give high selectivities to THF in the hydrogenation of MA.

Catalysts based on copper oxide and having a specific porosity and their use as hydrogenation catalysts are known per se.

Thus, U.S. Pat. No. 5,155,086 discloses pulverulent catalysts which comprise copper oxide, zinc oxide and aluminum oxide and in which at least 40% of the total pore volume is made up by pores having diameters of from 120 to 1000 Å. Such catalysts are suitable for the hydrogenation of carboxylic acids and carboxylic esters to alcohols and of ketones and aldehydes to alcohols. The hydrogenation of MA to THF is not described.

EP-A 604 792 describes catalysts which comprise, per 100 parts by weight of copper oxide, from 40 to 130 parts by weight of zinc oxide, from 2 to 50 parts by weight of aluminum oxide and from 1 to 40 parts by weight of sodium oxide and have a total surface area of from 50 to 100 $m^2/g$ (by the BET method), where from 75 to 95% of the total surface area is made up by pores having radii of from 9 to 1000 mm and the remaining surface area is made up by pores having a radius of <9 mm. Catalysts of this type are used for the hydrogenation of organic compounds, in particular for the hydrogenation of saturated and unsaturated aldehydes, ketones, carboxylic acids or carboxylic esters to saturated alcohols. The hydrogenation of MA to THF is not described.

Finally, WO 97/34694 discloses copper oxide/aluminum oxide hydrogenation catalysts which can be in extrudate form or in the form of pressed pellets. The extrudates have pore volumes of from 0.15 to 0.6 ml/g and bimodal pore radius distributions having maxima at about 100 Å and at 1000–2000 Å, while the pressed pellets have pore volumes of from 0.2 to 0.6 ml/g and bimodal pore radius distributions having maxima at about 100 Å and at 500–2000 Å. Here too, the hydrogenation of MA to THF is not mentioned.

The catalysts used according to the present invention differ from the catalysts described in the prior art. They comprise copper oxide and at least one further metal or compound, preferably an oxide, selected from the group consisting of Al, Si, Zn, La, Ce, the elements of groups IIIA to VIIIA and the elements of groups IA and IIA. Furthermore, the catalyst solids have a pore volume of $\geq 0.01$ ml/g for pore diameters of >50 nm and a ratio of the pore volume of macropores having a diameter of >50 nm to the total pore volume for pores having a diameter of >4 nm of >10%.

For the purposes of the present invention, the groups of the Periodic Table of the Elements are designated in accordance with the old IUPAC nomenclature.

The catalysts of the present invention allow the hydrogenation of $C_4$-dicarboxylic acids and/or their derivatives to be carried out so as to form THF as main product in yields of significantly above 90%, very frequently close to 100%.

For the purposes of the present invention, the term "$C_4$-dicarboxylic acids and their derivatives" refers to maleic acid or succinic acid which may be unsubstituted or bear one or more $C_1$–$C_4$-alkyl substituents and also the anhydrides and esters of these unsubstituted or alkyl-substituted acids. An example of such an acid is citraconic acid. Preference is given to using MA as starting material to be hydrogenated.

The THF prepared can also bear one or more alkyl substituents, depending on the starting material used. A THF substituted in this way will hereinafter be referred to as a THF derivative.

The catalysts of the present invention comprise, as base material, copper oxide admixed with at least one further metal or compound thereof, preferably an oxide. Use is made of a metal selected from the group consisting of Al, Si, Zn, Al, Ce, the elements of groups IIIA to VIIIA and the elements of groups IA and IIA or a compound thereof, preferably an oxide.

Preference is given to using silicon dioxide, zinc oxide, aluminum oxide, zirconium oxide and/or titanium dioxide. Particular preference is given to chromium-free systems based on copper oxide/aluminum oxide and copper oxide/zinc oxide/aluminum oxide.

The copper oxide content of the catalysts of the present invention is $\geq 10\%$ by weight, preferably $\geq 25\%$ by weight.

In order to display the desired properties in respect of hydrogenation activity, the catalysts of the present invention have to have specific properties in respect of the porosity. The catalysts used as shaped bodies have a pore volume of $\geq 0.01$ ml/g for pore diameters of >50 nm, preferably $\geq 0.025$ ml/g for pore diameters of >100 nm and in particular $\geq 0.05$ ml/g for pore diameters of >200 nm. These values were determined by mercury intrusion in accordance with DIN 66133. The data were evaluated in the pore diameter range from 4 nm to 300 $\mu$m.

Furthermore, the presence of a certain macroporosity is important. Thus, the ratio of the pore volume of macropores having a diameter of >50 nm to the total pore volume for pores having a diameter of >4 nm in the shaped body should be >10%. This ratio is preferably>20%, in particular >30%.

The catalyst composition is prepared by methods known to those skilled in the art. Preference is given to methods in which the copper oxide is obtained in finely divided form intimately mixed with the other constituents. This is preferably achieved by precipitation reactions. Here, copper compounds dissolved in a solvent are precipitated by means of a precipitant in the presence of further metal compounds dissolved or suspended in the solvent, filtered off, washed, dried and, if desired, calcined.

For example, the corresponding metal carbonates and/or hydroxides can be precipitated in aqueous solution, filtered off, washed, dried and, if desired, calcined. The metal carbonates or hydroxides are obtainable, for example, by dissolving the corresponding metal salts in water and adding sodium carbonate solution. Metal salts used are, for example, nitrates, sulfates, chlorides, acetates and/or oxalates.

The catalysts of the present invention are in the form of shaped bodies known to those skilled in the art. Examples of suitable shaped bodies include pressed pellets, rings, spheres and extrudates. These shaped bodies can be obtained by known methods, for example extrusion, tabletting or agglomeration processes.

The porosity which the catalysts of the present invention have to have to achieve the desired hydrogenation activity can be obtained by means of particular measures during their production. Examples of such measures are the addition of pore formers, additives, the choice of a suitable particle size distribution and porosity of the catalyst powder, suitable process parameters in the shaping of the starting materials or a combination of the abovementioned measures.

Suitable pore formers are, for example, carboxylic acids such as oxalic acid, stearic acid and palmitic acid, also carbohydrates and modified carbohydrates such as starch and methylcellulose. Further suitable pore formers are powdered activated carbons, graphite, ammonium salts and nitrates. These substances can be removed again after shaping, for instance by heat treatment of the shaped catalyst body.

As additives for adjusting the porosity which remain permanently in the catalyst, it is possible to use, for example, metal oxides, metal carbides and metal nitrides.

A suitable particle size distribution and porosity of the catalyst powder can be achieved, for example, by thermal pretreatment of a suspension of catalyst powder. In the shaping of the catalyst, it is possible, for example, to achieve a higher macroporosity by means of a low energy input during pan milling or reduced pressing pressures during tabletting.

The use of precalcined starting materials and the use of pore formers is preferred for setting the catalyst porosity according to the present invention.

As an alternative to the above-described methods of preparation, the catalysts of the present invention can also be produced, for example, by applying the active component to a support having an appropriate porosity. Application can be carried out, for example, by impregnation. Catalysts according to the present invention can also be obtained by shaping a heterogeneous mixture of active component or precursor compounds thereof with a support component or precursor compounds thereof.

The catalysts used may further comprise an auxiliary in an amount of from 0 to 10% by weight. For the purposes of the present invention, auxiliaries are organic and inorganic materials which contribute to improved processing during catalyst production and/or to an increase in the mechanical strength of the shaped catalyst bodies. Such auxiliaries are known to those skilled in the art; examples include graphite, stearic acid, silica gel and copper powder.

In general, the catalyst is subjected to activation, generally a pretreatment with hydrogen, before use in the reaction. This produces the active catalyst species by partial reduction of the compounds present in the catalyst mixture, in particular the copper oxides, to the elemental metal or lower oxidation states of the metal which is active in the catalytic reaction carried out according to the present invention.

The catalyst of the present invention has a satisfactory operating life. Should the activity and/or selectivity of the catalyst nevertheless decrease during its time in operation, it can be regenerated by means of measures known to those skilled in the art. These include reductive treatment of the catalyst in a stream of hydrogen at elevated temperature. The reductive treatment can optionally be preceded by an oxidative treatment. Here, a gas mixture comprising molecular oxygen, for example air, is passed through the catalyst bed at elevated temperature. It is also possible to wash the catalyst with a suitable solvent, for example methanol, THF or GBL, and subsequently to dry it by means of a stream of gas.

Reactors suitable for carrying out the reaction are reactors in general in which the catalyst is located as a fixed bed. Preference is given to shell-and-tube reactors so that the heat liberated in the reaction can readily be removed. In the hydrogenation, the starting material, preferably MA, is vaporized and passed through the reactor together with a hydrogen-containing stream of gas. Preference is given to using pure hydrogen. The addition of other gaseous components, for example water vapor or carbon monoxide, can have a favorable effect on the selectivity, activity or long-term stability. The concentration of the starting material is preferably in the range from 0.2 to 2% by volume. At significantly higher concentrations of starting material, the starting material condenses in the reactor, particularly when using MA, and coats the catalyst with a liquid film. Significantly lower concentrations would reduce the space-time yield.

The reaction temperature is from 150 to 400° C., preferably from 200 to 300° C. Higher temperatures promote the formation of by-products, while lower temperatures lead to an unnecessary decrease in the activity of the catalyst. The pressure is from 0.5 to 100 bar, preferably from 1 to 50 bar, in particular <20 bar. The GHSV (gas hourly space velocity= volume flow of the reaction gas at STP divided by the volume of the catalyst bed) is set so that complete conversion of the starting material is achieved. This aids the work-up of the product mixture and saves recirculation of unreacted starting material. For this purpose, the GHSV is set to from 10 to 50,000 $h^{-1}$, preferably from 100 to 10,000 $h^{-1}$. The product mixture can be separated by methods known to those skilled in the art. Part of the unreacted hydrogen is preferably circulated and thus reused in the hydrogenation.

The invention is illustrated by the following examples.

EXAMPLE 1
Production of a Catalyst According to the Present Invention 8.1 l of water and 672 g of boehmite (Pural® SB, from Condea, $Al_2O_3$ content: about 72%) are placed in a heatable precipitation vessel provided with a stirrer and are heated to 50° C. 7.5 of a metal salt solution comprising 2980 g of $Cu(NO_3)_2 * 3H_2O$ and 3560 g of $Zn(NO_3)_2 * 6H_2O$ and at the same time a 20% strength by weight solution of sodium carbonate are metered into this precipitation vessel over a period of half an hour while stirring. The sodium carbonate solution is metered in in such an amount that a pH of 6.2 is established in the precipitation vessel. The consumption of sodium carbonate solution is 13.8 kg. The suspension formed is filtered and the solid is washed with water until the washings no longer contain any nitrate (<25 ppm). The filter cake is firstly dried at 120° C. and subsequently calcined at 300° C.

1.7 kg of this material are intensively mixed with 300 g of ammonium nitrate and 60 g of graphite and tabletted to produce pellets having a diameter of 3 mm and a height of 3 mm. The pellets are calcined at 500° C. for two hours.

EXAMPLE 2
Production of a Catalyst According to the Present Invention 1.9 kg of the precipitated product from Example 1 are intensively mixed with 100 g of ammonium nitrate and 60 g of graphite and pressed to produce pellets having a diameter of 3 mm and a height of 3 mm. The pellets are calcined at 500° C. for two hours.

EXAMPLE 3
Production of a Catalyst According to the Present Invention 1.7 kg of the product precipitated as described in Example 1 and dried at 120° C. are calcined at 800° C. and subsequently intensively mixed with 300 g of the uncalcined precipitated product and 60 g of graphite and tabletted to produce tablets having a diameter of 3 mm and a height of 3 mm.

Comparative Example 1
Production of a Catalyst 1.5 kg of the precipitated product dried at 120° C. and calcined at 300° C. from Example 1 are intensively mixed with 45 g of graphite and tabletted to produce pellets having a diameter of 3 mm and a height of 3 mm.

EXAMPLES 4 TO 6, COMPARATIVE EXAMPLE 2

Hydrogenation of Maleic Anhydride 100 ml of the catalyst pellets from the above examples were mixed with 100 ml of glass rings of the same size and placed in a tube reactor having an internal diameter of 27 mm. The reactor was heated/cooled by circulating oil and the reaction gas was passed through it from the top downward. The interior of the catalyst bed had an axial temperature profile. MA was pumped as melt into a vaporizer operated at 200° C. where it was vaporized in a stream of hydrogen. The MA/hydrogen mixture having an MA concentration of 1.2% by volume was then passed through the reactor and preheated above the catalyst bed. The conversion of MA was complete in all examples.

Before the MA/hydrogen mixture was fed into the reactor, the catalyst was subjected to a pretreatment with hydrogen. For this purpose, the reactor was firstly flushed with 200 standard 1/h of nitrogen at atmospheric pressure and at the same time heated over a period of 1 hour to a temperature in the catalyst bed of 180° C. The nitrogen flow was then increased to 950 standard 1/h and an additional 50 standard 1/h of hydrogen was fed in. During this procedure, a slight temperature increase in the catalyst bed to about 250° C. in the hot spot was observed. The hot spot migrates through the reactor from the reactor inlet to the end of the reactor. After the temperature in the entire catalyst bed had cooled to 190° C., the nitrogen flow was reduced to 900 standard 1/h and the amount of hydrogen was increased to 100 standard 1/h . The nitrogen flow was gradually switched off, and the hydrogen flow was gradually increased to 600 standard 1/h .

As can be seen from the table, significantly higher THF selectivities can be achieved when using the catalysts of the present invention than when using the comparative catalyst.

TABLE

| Ex. No. | Catalyst No. | Pore volume 4 nm < d < 300 μm [cm³/g] | Pore volume 50 nm < d < 300 μm [cm³/g] | Proportion of macropores d < 50 nm/d < 2 nm [%] | T [° C.] | $S_{GBL}$ [mol %] | $S_{THF}$ [mol %] | $S_{remainder}$ [mol %] |
|---|---|---|---|---|---|---|---|---|
| 4 | 1 | 0.392 | 0.233 | 59% | 260 | 0 | 98 | 2 |
| 5 | 2 | 0.354 | 0.139 | 39% | 250 | 1 | 97 | 2 |
| 6 | 3 | 0.127 | 0.045 | 35% | 250 | 2 | 96 | 2 |
| Comp. Ex. 2 | Comp. Ex. 1 | 0.187 | 0.007 | 3.7% | 260 | 12 | 78 | 10 |

$S_{XXX}$ = Selectivity

We claim:

1. The method of using a substantially chromium free hydrogenation catalyst comprising copper oxide and at least one further metal or compound thereof, selected from the group consisting of Al, Si, Zn, La, Ce, the elements of groups IIIA to VIIIA and the elements of groups IA and IIA and having a pore volume of ≧0.01 ml/g for pore diameters of >50 nm and a ratio of the pore volume of macropores having a diameter of >50 nm to the total pore volume for pores having a diameter of >4 nm of >10%, in the hydrogenation of $C_4$-dicarboxylic acids or their derivatives in the gas phase to form THF or its derivatives.

2. The method as claimed in claim 1, wherein the metal compound is an oxide.

3. The method as claimed in claim 1, wherein the $C_4$-dicarboxylic acid is maleic acid.

4. The method as claimed in claim 1, wherein the further metal oxide is selected from the group consisting of silicon dioxide, zinc oxide, aluminum oxide, zirconium oxide and titanium dioxide.

5. The method as claimed in claim 4, wherein the catalyst is selected from among copper oxide/aluminum oxide mixtures and copper oxide/zinc oxide/aluminum oxide mixtures.

6. The method as claimed in claim 1, wherein the copper oxide content is ≧10% by weight.

7. The method according to claim 6, wherein the copper oxide content is ≧25% by weight.

8. The method as claimed in claim 1, wherein the pore volume is ≧0.025 ml/g for diameters of >100 nm.

9. The method according to claim 8, wherein the pore volume is ≧0.05 ml/g for pore diameters of >200 nm.

10. The method as claimed in claim 1, wherein the ratio of the pore volume of macropores having a diameter of >50 nm to the total pore volume for pores having a diameter of >4 nm is >10%.

11. The method as claimed in claim 10, wherein the ratio is >20%.

12. The method as claimed in claim 11, wherein the ratio is >30%.

13. The method as claimed in claim 1, wherein the catalyst is in the form of shaped bodies.

14. The method as claimed in claim 13, wherein the catalyst is in the form of pressed pellets, rings, spheres or extrudates.

15. The method as claimed in claim 1, wherein the hydrogenation is carried out at from 150 to 400° C., pressures of from 0.5 to 100 bar, GHSVs of from 10 to 50,000 $h^{-1}$, and concentrations of the $C_4$-carboxylic acid or the derivative thereof of from 0.2 to 2% by volume.

16. The method as claimed in claim 15, wherein the temperature is from 100 to 300° C.

17. The method as claimed in claim 15, wherein the pressure is from 1 to 50 bar.

18. The method as claimed in claim 15, wherein the pressure is <20 bar.

19. The method as claimed in claim 15, wherein the GHSV's are from 100 to 10,000 $h^{-1}$.

* * * * *

UNITED STATES PATENT AND TRADEMARK OFFICE
CERTIFICATE OF CORRECTION

PATENT NO.        : 6,888,011 B2                                              Page 1 of 1
APPLICATION NO.   : 10/433012
DATED             : May 3, 2005
INVENTOR(S)       : Borchert et al.

It is certified that error appears in the above-identified patent and that said Letters Patent is hereby corrected as shown below:

Title page, item [30]
Foreign Application Priority Data (date) is --Dec. 11, 2000-- not "Dec. 11, 2001".

Signed and Sealed this

Twenty-second Day of May, 2007

JON W. DUDAS
*Director of the United States Patent and Trademark Office*